US012778614B2

(12) United States Patent
Li et al.

(10) Patent No.: US 12,778,614 B2
(45) Date of Patent: Nov. 3, 2026

(54) PERFUSION AND SUCTION SYSTEM AND PERFUSION AND SUCTION CONTAINER

(71) Applicant: ZHEJIANG YIGAO MEDICAL TECHNOLOGY CO., LTD., Zhejiang (CN)

(72) Inventors: Fangbing Li, Zhejiang (CN); Penghong Xu, Zhejiang (CN); Jinpin Chen, Zhejiang (CN)

(73) Assignee: ZHEJIANG YIGAO MEDICAL TECHNOLOGY CO., LTD., Zhejiang (CN)

( * ) Notice: Subject to any disclaimer, the term of this patent is extended or adjusted under 35 U.S.C. 154(b) by 118 days.

(21) Appl. No.: 19/006,241

(22) Filed: Dec. 31, 2024

(65) Prior Publication Data

US 2025/0127532 A1 Apr. 24, 2025

Related U.S. Application Data

(63) Continuation of application No. PCT/CN2023/100677, filed on Jun. 16, 2023.

(51) Int. Cl.
*A61B 17/22* (2006.01)
*A61B 17/225* (2006.01)
(Continued)

(52) U.S. Cl.
CPC *A61B 17/2251* (2013.01); *A61B 2017/00084* (2013.01); *A61B 2017/22079* (2013.01); *A61B 2090/064* (2016.02); *A61B 2217/007* (2013.01)

(58) Field of Classification Search
CPC .............. A61B 17/225; A61B 17/2251; A61B 2017/22079; A61B 2217/007
See application file for complete search history.

(56) References Cited

U.S. PATENT DOCUMENTS

2014/0324065 A1* 10/2014 Bek .................. A61B 17/32002 606/110
2022/0202285 A1 6/2022 Bukesov et al.

FOREIGN PATENT DOCUMENTS

CN 102281830 12/2011
CN 106963344 7/2017
(Continued)

OTHER PUBLICATIONS

English Translation of CN 110638491 A (Year: 2020).*
"International Search Report (Form PCT/ISA/210) of PCT/CN2023/100677," mailed on Feb. 18, 2024, pp. 1-6.

*Primary Examiner* — Tuan V Nguyen
(74) *Attorney, Agent, or Firm* — JCIPRNET

(57) ABSTRACT

The present disclosure provides a perfusion and suction system, the host controller thereof is configured to execute a constant pressure regulation method including the following steps. A pressure detection device collects the pressure in a cavity and transmits it to the host controller, the host controller adjusts perfusion and suction parameters according to the real-time monitored pressure value and the data change trend of the pressure value, so that the current pressure in the cavity is balanced at a pressure control value, thus realizing a balance state between perfusion and suction; the perfusion parameters include a perfusion flow gear, and the suction parameters include an opening threshold of a relief valve and a suction pressure threshold; the suction pressure threshold is a suction pressure threshold of the suction container preset by the host controller, and the on-off of the suction pump is controlled by setting the suction pressure threshold.

10 Claims, 7 Drawing Sheets

(51) Int. Cl.
*A61B 90/00* (2016.01)
*A61B 17/00* (2006.01)

(56) References Cited

FOREIGN PATENT DOCUMENTS

| | | | | |
|---|---|---|---|---|
| CN | 110638491 A | * | 1/2020 | ....... A61B 17/00234 |
| CN | 110639070 | | 1/2020 | |
| CN | 111870342 | | 11/2020 | |
| CN | 113577402 | | 11/2021 | |
| CN | 114452011 | | 5/2022 | |
| CN | 217593042 | | 10/2022 | |
| CN | 115670646 | | 2/2023 | |
| CN | 221286426 | | 7/2024 | |

* cited by examiner

PERFUSION AND SUCTION SYSTEM AND PERFUSION AND SUCTION CONTAINER

CROSS-REFERENCE TO RELATED APPLICATION

This application is a continuation of international application of PCT application serial no. PCT/CN2023/100677, filed on Jun. 16, 2023. The entirety of the above-mentioned patent applications is hereby incorporated by reference herein and made a part of this specification.

TECHNICAL FIELD

The present disclosure relates to the field of ureteral flexible endoscope lithotripsy, in particular to a perfusion and suction system and a constant pressure and temperature control method thereof.

BACKGROUND

In a conventional ureteral lithotripsy with flexible endoscopy, the powder of stones and hematuria in renal pelvis can lead to blurred vision, which requires perfusion solution to maintain clear vision. However, at the same time, the intrapelvic pressure will increase significantly due to rapid perfusion and poor return, causing infected urine, bacteria and endotoxin to enter the blood and lymphatic circulation, resulting in postoperative fever, systemic inflammatory response syndrome and even fatal urogenous sepsis in patients. In order to prevent severe infection caused by excessive pressure in the renal pelvis during a flexible contact lenses surgery, it is necessary to control the intraoperative pressure within a safe range. It is further necessary to feedback and adjust the perfusion flow rate and/or negative suction value according to the intraoperative pressure of the renal pelvis. Whether the manometric method used can measure the pressure of the renal pelvis in real time and accurately is the cornerstone to ensure the good performance of the system and the safety of surgical operation.

At present, the conventional pressure regulation method is to adjust the intracavity pressure by adjusting the perfusion flow rate, and the suction unit is not used to adjust the pressure at the same time. Due to the large suction effect of the suction pump, reducing the perfusion flow rate will cause the pressure to drop too fast and not be stable at the ideal pressure value. The ideal pressure value in the renal pelvis during surgery needs to be 8-12 mmHg. The surgical environment is complex, and the pressure in the renal pelvis always fluctuates. At present, the regulation of pressure is extensive and it cannot be adjusted to an appropriate ideal pressure. In addition, the tissue loss caused by sudden temperature increase due to laser lithotripsy cannot be reduced in time only by reducing the temperature through perfusion and suction circulation. In view of the short duration of surgery and extremely high temperature, the surgical risk is great.

SUMMARY OF INVENTION

The present disclosure provides a perfusion and suction system. The perfusion and suction system includes a sheath tube, an endoscope, a perfusion unit, a suction unit, a host controller and a pressure sensor; a suction channel is provided in the sheath tube, the endoscope is inserted in the sheath tube, and a liquid delivery channel is formed in the endoscope; the pressure sensor is disposed in either the endoscope, the sheath tube or a perfusion pump, the pressure sensor is used for detecting a pressure inside a body cavity, and the perfusion unit communicates with the liquid delivery channel for injecting a perfusion solution into the body cavity; the suction unit includes a suction pump and a suction container connected with the suction pump, the suction container is provided with a pressure relief valve, the suction container communicates with the suction channel for sucking out liquid in the body cavity, and the perfusion unit cooperates with the suction unit to keep the cavity at an appropriate pressure; the host controller is communicatively connected with the pressure sensor, the perfusion unit and the suction unit.

The host controller is configured to execute a constant pressure control method, and the constant pressure control method includes the following steps: step 1), preset a highest warning pressure value, a lowest warning pressure value, a pressure control value and a perfusion flow gear; step 2), the host controller controls the perfusion unit to send the perfusion solution into the body cavity, and is able to control the suction unit to pump out the liquid in the body cavity; and step 3), a pressure detection device collects the pressure in a cavity and transmits it to the host controller, the host controller adjusts perfusion and suction parameters according to the real-time monitored pressure value and the data change trend of the pressure value, so that the current intracavity pressure is balanced at a pressure control value, thus realizing a balance state between perfusion and suction; the perfusion parameters include a perfusion flow gear, and the suction parameters include an opening threshold of a relief valve and a suction pressure threshold; the suction pressure threshold is a suction pressure threshold of the suction container preset by the host controller, and the on-off of the suction pump is controlled by setting the suction pressure threshold; the constant pressure control of the host controller includes a coarse tuning mode, a fine tuning mode and a mixed tuning mode, the coarse tuning mode is in response to the intracavity pressure exceeding the highest warning pressure value and the lowest warning pressure value; the fine tuning mode is in response to the pressure difference between the intracavity pressure and the pressure control value being at a first level; the mixed tuning mode is in response to the pressure difference between the intracavity pressure and the pressure control value being at a second level, and the pressure difference at the second level is greater than the pressure difference at the first level; the coarse tuning mode includes the steps of tuning the perfusion flow gear and the way to open the relief valve in response to the pressure exceeding the highest warning pressure value and the lowest warning pressure value; the fine tuning mode includes the steps of maintaining the perfusion gear to maintain operation and keeping the relief valve closed, and performing pressure adjustment by finely tuning the suction pressure threshold; and the mixed tuning mode includes the steps of combining fine tuning of the perfusion flow, fine tuning of the relief valve and fine tuning of the suction pressure threshold to jointly act on the intracavity pressure through jointly tuning the perfusion flow gear, the relief valve and the suction pressure threshold, so as to achieve the effect of supercharging or pressure reduction.

Preferably, when the pressure difference between the intracavity pressure and the pressure control value exceeds ±20 mmHg, the coarse tuning mode is activated; when the pressure difference exceeds ±3 mmHg and is within ±8 mmHg, the fine tuning mode is activated; when the detected pressure difference exceeds #8 mmHg and is within ±20 mmHg, the mixed tuning mode is activated.

Preferably, the coarse tuning mode includes the following steps: when the pressure value in the body cavity exceeds the highest warning line, the host controller controls to lower the perfusion flow gear, controls the suction pressure threshold so that the suction flow rate is greater than the perfusion flow rate; when the pressure difference in the cavity exceeds the lowest warning line, the perfusion flow gear will be increased, the relief valve will be opened, and the suction pressure threshold will be tuned to a threshold in a stable state, a rapid balance effect is achieved, so that the intracavity pressure can be free from an extreme state as soon as possible.

Preferably, when the pressure difference exceeds −3 mmHg and is within −8 mmHg, keep the perfusion flow gear unchanged, keep the relief valve closed, maintain the current operation of perfusion, observe the change trend of uploaded data, increase the suction pressure threshold if it is in an ascending stage, decrease the suction pressure threshold if it is in a descending trend, and the reduction amplitude is greater than the amplitude of increasing the suction pressure threshold in the ascending stage; in this way, in the process of data adjustment, the suction pressure threshold tends to be decreased as a whole to achieve the effect of supercharging by fine tuning; when the pressure difference exceeds 3 mmHg and is within 8 mmHg, keep the perfusion operating at the current level; observe the change trend of uploaded data, increase the "suction pressure threshold" if it is in an ascending stage, decrease the suction pressure threshold if it is in a descending trend, and the reduction amplitude is smaller than the amplitude of increasing the suction pressure threshold in the ascending stage; in the process of data adjustment, the "suction pressure threshold" tends to be increased as a whole to achieve the effect of pressure reduction.

Preferably, wherein when the detected pressure difference exceeds 8 mmHg and is within 20 mmHg, appropriately reduce the perfusion flow rate, observe the change trend of uploaded data, increase the suction pressure threshold if it is in an ascending stage, and decrease the suction pressure threshold if it is in a descending state, and the reduction amplitude is smaller than the amplitude of increasing the suction pressure threshold in the ascending stage; in this way, in the process of data adjustment, the "suction pressure threshold" tends to be increased as a whole to achieve the effect of pressure reduction; when the pressure difference is detected lower than-8 mmHg and is within −20 mmHg, keep the perfusion flow rate at the current level, open the relief valve in stages, observe the change trend of uploaded data, increase the suction pressure threshold if it is in an ascending stage, decrease the "suction pressure threshold" if it is in a descending trend, and the reduction amplitude is greater than the amplitude of increasing the suction pressure threshold in the ascending stage; in this way, in the process of data adjustment, the "suction pressure threshold" tends to be decreased as a whole to achieve the effect of supercharging.

Preferably, wherein the amplitude of tuning the suction pressure threshold increases with an increase in the pressure difference between the intracavity pressure and the pressure control value.

Preferably, the perfusion unit further includes: a perfusion pump for pumping the perfusion solution; a room-temperature liquid storage bag for storing the room-temperature perfusion solution; a low-temperature liquid storage bag for storing the low-temperature perfusion solution; a room-temperature liquid inlet tube, with the room-temperature liquid storage bag being connected with the room-temperature liquid inlet tube; a low-temperature liquid inlet tube, with the low-temperature liquid storage bag being connected with the low-temperature liquid inlet tube; a temperature sensor provided on the endoscope or the sheath to detect a temperature in the body cavity; a mixing tubeline, one end of which being communicated with the outlets of the room-temperature liquid inlet tube and the low-temperature liquid inlet tube, and the other end thereof being connected with the perfusion pump; a proportion control valve for controlling liquid flow rates of the room-temperature liquid inlet tube and the low-temperature liquid inlet tube; the host controller controls a mixing ratio of the room-temperature perfusion solution and the low-temperature perfusion solution according to a temperature signal obtained by the temperature sensor, thereby controlling a supply temperature of the perfusion solution; the temperature control method includes: step 1), preset a first predetermined temperature $T_{max}$ and a second predetermined temperature $T_{min}$, wherein the room-temperature storage liquid has a first predetermined temperature t1 and the low-temperature storage liquid has a second predetermined temperature t2; step 2), after each temperature acquisition, compare the acquired temperature T with the first predetermined temperature $T_{max}$ and the second predetermined temperature $T_{min}$; if the acquired temperature T is higher than the first predetermined temperature $T_{max}$ or lower than the second predetermined temperature $T_{min}$, the control valve connects the room-temperature liquid storage bag with the mixing tubeline, connects the low-temperature liquid storage bag with the mixing tubeline, or controls the mixing ratio of the room-temperature liquid inlet tube and the low-temperature liquid inlet tube according to the temperature difference between the acquired temperature and a desired temperature, further controlling the output liquid temperature of the mixing tubeline; and step 3) if it is judged that T reaches an ideal temperature, the temperature control process will be stopped; if not, the opening of the proportion control valve will be further adjusted in real time according to the temperature difference until the ideal temperature is reached.

Preferably, the perfusion unit includes: a low-temperature perfusion pump connected with the low-temperature liquid inlet tube; a room-temperature perfusion pump connected with the room-temperature liquid inlet tube, and communicated with the liquid outlet tube after being merged with the liquid outlet of the low-temperature perfusion pump; the temperature control method includes: step 1), preset a first predetermined temperature $T_{max}$ and a second predetermined temperature $T_{min}$, wherein the room-temperature storage liquid has a first predetermined temperature t1 and the low-temperature storage liquid has a second predetermined temperature t2; step 2), after each temperature acquisition, compare the acquired temperature T with the first predetermined temperature $T_{max}$ and the second predetermined temperature $T_{min}$; if the acquired temperature T is higher than the first predetermined temperature $T_{max}$ or lower than the second predetermined temperature $T_{min}$, the host controller controls the rotation speed ratio of the room-temperature perfusion pump to the low-temperature perfusion pump respectively to adjust the flow rates of the room-temperature liquid inlet tube and the low-temperature liquid inlet tube; and step 3), if it is judged that T reaches an ideal temperature, the temperature control process will be stopped; if not, the rotation speed ratio of the room-temperature perfusion pump to the low-temperature perfusion pump will be further adjusted in real time according to the temperature difference until the ideal temperature is reached.

The present disclosure further provides a perfusion and suction container, including a suction unit and a perfusion unit, wherein the perfusion unit includes a perfusion pump for pumping the perfusion solution; a room-temperature liquid storage bag for storing the room-temperature perfusion solution; a low-temperature liquid storage bag for storing the low-temperature perfusion solution; a room-temperature liquid inlet tube, with the room-temperature liquid storage bag being connected with the room-temperature liquid inlet tube; a low-temperature liquid inlet tube, with the low-temperature liquid storage bag being connected with the low-temperature liquid inlet tube; the suction container includes a suction pump, a first negative pressure suction tube, a suction container and a second negative pressure suction tube, wherein one end of the first negative pressure suction tube is connected with the suction pump and the other end thereof is connected with the suction container, and one end of the second negative pressure suction tube is connected with the suction container and the other end thereof is connected with the sheath tube; a host controller communicatively connected with the perfusion unit and the suction unit.

Preferably, the perfusion pump, a diaphragm pump and the host controller are integrated.

According to the present disclosure, a relief valve is arranged in the suction container and a suction pressure threshold is set, so that a coarse tuning mode, a fine tuning mode and a mixed tuning mode are realized through the suction unit, thus realizing real-time adjustment of the pressure in the body cavity, making the pressure dynamically balanced at a pressure control value, and reducing damage to body cavity tissues caused by pressure fluctuation; at the same time, the present disclosure judges the current state of the detected pressure value in the body cavity and the data change trend, and dynamically adjusts the pressure in the body cavity in combination with multiple modes. Further, the perfusion and suction system provided by the present disclosure realizes accurate control of the temperature in the cavity by controlling the temperature of the perfusion solution at the source. Compared with only relying on the adjustment of perfusion flow rate, this embodiment first reduces the excessive requirement for perfusion flow rate and controls the temperature more accurately and in real time, thus reducing the experience requirements of the surgeon and reducing postoperative complications. The system provided by the present disclosure adjusts the pressure, flow rate and temperature of perfusion in a timely manner through dual monitoring of the pressure and temperature in the cavity, thereby effectively improving the safety of surgery and reducing the risk caused by excessively high or low temperature and pressure during surgery.

DESCRIPTION OF EMBODIMENTS

Figure 1:
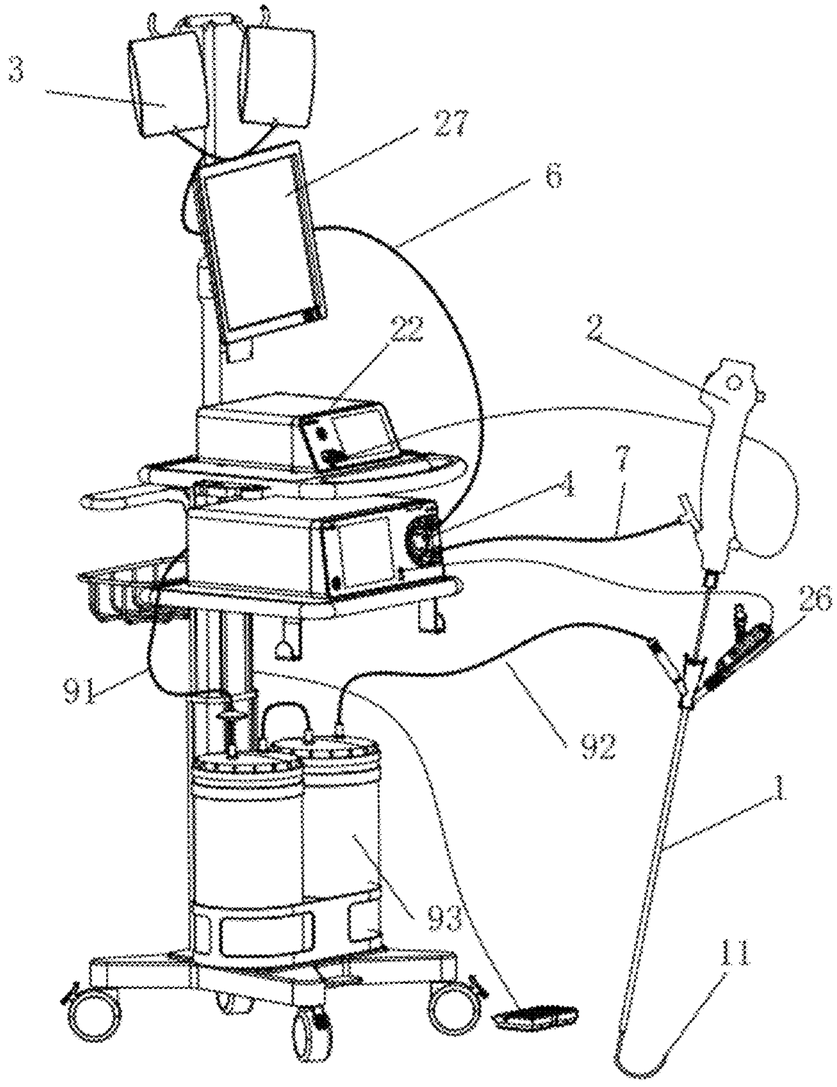
FIG. 1 is a structural schematic diagram of a perfusion and suction system provided by the present disclosure.

In the description of the present disclosure, it should be understood that the azimuth or positional relationships indicated by terms such as “upper”, “lower”, “front”, “rear”, “left”, “right”, “inside”, “outside”, “proximal” and “distal” are based on those shown in the drawings, which are only for facilitating the description of the present disclosure and simplifying the description, rather than indicating or implying that the target device or component must have a specific orientation and be structured and operated at a specific orientation. Therefore, it cannot be construed as a limitation of the present disclosure. In addition, the features defined as “first” and “second” may explicitly or implicitly include one or more of such features.

Embodiment 1

As shown in FIG. 1, the present embodiment provides a perfusion and suction system under intelligent constant pressure control. The system includes a sheath tube 1, an endoscope 2, a perfusion unit, a suction unit, a pressure sensor and a host controller. The sheath tube 1 further has a suction channel, and in this embodiment, the suction channel and the main channel are the same channel; the endoscope 2 is inserted into the sheath tube 1, and a liquid delivery channel is formed in the endoscope 2; the perfusion unit 10 communicates with the liquid delivery channel for injecting the perfusion solution into the body cavity.

The suction unit is used for pumping out the waste liquid and stones in the cavity through a negative pressure of a sheath tube, collecting the waste liquid and stones into an suction container through a negative pressure suction tube, and maintaining the cavity at a proper pressure by cooperating with the perfusion unit and the suction unit; specifically, the suction unit is connected with the sheath tube 1. The suction unit includes a diaphragm pump, a first negative pressure suction tube 91, a suction container 93 and a second negative pressure suction tube 92. One end of the first negative pressure suction tube 91 is connected with the diaphragm pump and the other end thereof is connected with the suction container 93; one end of the second negative pressure suction tube 92 is connected with the suction container 93 and the other end thereof is connected with the sheath tube 1; specifically, when a laser operation is performed for a long time and the operation lasts for a long period of time, the perfusion solution will be relatively increased, the suction unit can be used to reduce the intracavity pressure.

The perfusion unit includes a liquid inlet tube 6, a liquid storage bag 3 and a perfusion pump 4; the perfusion pump 4 is connected with the liquid storage bag 3 through the liquid inlet tube 6; the perfusion pump 4 is communicated with a liquid delivery channel 8 of the endoscope through a liquid outlet tube 7; and the suction unit includes a suction pump, a first negative pressure suction tube 91, a suction container 93, a second negative pressure suction tube 92 and a pressure sensor; one end of the first negative pressure suction tube 91 is connected with the sheath tube 1 and the other end thereof is connected with the suction container 93; one end of the second negative pressure suction tube 92 is connected with the suction container 93 and the other end thereof is connected with the suction pump; the pressure sensor is used for detecting the intracavity pressure in the suction container 93, and the suction container 93 is provided with a relief valve.

The host controller is communicatively connected with the pressure sensor, the perfusion unit and the suction unit. The host controller controls the flow rate and pressure of the perfusion unit and the suction unit according to the pressure value output by the pressure sensor. In this embodiment, the perfusion pump and the suction pump are integrated with the host controller and installed in the housing 5. Optionally, the perfusion pump is a peristaltic pump, and the suction pump is a diaphragm pump.

It can be understood that the host controller may be installed on an endoscope or on an image processor 22.

The pressure sensor can be arranged at the distal end of the endoscope, or at the distal end of the sheath tube, and more preferably at the proximal end of the sheath tube. In this embodiment, the pressure sensor 26 is arranged at the proximal end of the sheath tube, thus solving the problem that the pressure detection tubeline is too long with a high error; in actual operation, since all the sheath tubes are located in the cavity, physicians will not touch the sheath tube by mistake, thus avoiding the pressure detection error caused by a physician's accidental collision with the pressure detection tubeline. At the same time, it solves the problem of instantaneous high pressure caused by installing the pressure sensor at the distal end of the sheath tube; and the pressure sensor 26 is connected with the host controller.

The system also includes a display 27, the display 27 is capable of displaying pressure output values.

In one embodiment of the present disclosure, the present disclosure provides an intelligent constant pressure control method, which includes the following steps:

step 1), the pressure of a pressure detection device is output to a host controller, and the host controller compares the pressure with a preset ideal pressure; if the pressure fails to reach the ideal pressure, the parameters of perfusion and suction, proportional pressure, temperature and flow rate are controlled by the host controller; and step 2), the pressure detection device is provided with a control button, which can be used to directly control the perfusion unit and the suction unit to regulate the pressure in the body cavity.

In a preferred embodiment of the present disclosure, the suction unit further includes a suction pressure sensor, which is used to detect the intracavity pressure of the suction container 93. The suction container 93 is provided with a relief valve, and the host controller presets a suction pressure threshold. When the pressure of the suction container 93 is greater than the suction pressure threshold, the suction pump stops; when the pressure of the suction container is less than the suction pressure threshold and the current cavity pressure is greater than "pressure control value-3 mmHg", the suction pump starts. The pressure of the suction container is adjusted by changing the suction pressure threshold, and different pressures of the suction containers lead to different suction flow rates. By adjusting the suction flow rate and the perfusion flow rate, a certain intracavity pressure is maintained to achieve a dynamic balance between perfusion and suction.

The host controller controls the change of the suction pressure threshold to further control the pressure in the body cavity by controlling the pressure of the suction container. Compared with the magnitude of the suction pressure directly through the suction pump, the fine tuning of the pressure in the body cavity and the significant reduction of the pressure fluctuation in the body cavity can be realized through the suction pressure threshold.

The host controller further presets a highest warning pressure value, a lowest warning pressure value, a pressure control value and a perfusion flow gear. Here, the "pressure control value" refers to the ideal pressure value or pressure range in the preset cavity, and the "warning pressure value" here refers to the state that the difference between the intracavity pressure and the pressure control value exceeds this value. The pressure detection device detects the intracavity pressure every 0.25 s. When the intracavity pressure is not at the "pressure control value ±8 mmHg", it indicates that the pressure is higher or lower than the "pressure control value" at this time, and the pressure difference is too large. At this time, it is necessary to adjust the pressure in a wide range by coarse tuning, such as tuning the perfusion gear and tuning the relief valve to quickly regulate the intracavity pressure close to or reach the pressure control value. However, when the intracavity pressure is at a "pressure control value ±8 mmHg", the difference between the intracavity pressure and the pressure control value is small. If it continues to be adjusted by coarse tuning of such as perfusion gear or relief valve, it will easily cause the intracavity pressure to go to the other extreme, making it difficult to reach or approach the control value. In addition, the suction pressure of the suction pump of the suction unit is relatively large, and it is also difficult to achieve the effect of fine tuning if the pressure is directly adjusted by the suction pump. Based on this, the present disclosure finely tunes the pressure threshold value of the suction container; to sum up, the purpose of the present disclosure is to obtain a dynamic balance of intracavity pressure, and maintain the intracavity pressure at a dynamic balance state of the pressure control value through the combination of coarse tuning and fine tuning.

The present disclosure provides a constant pressure control method for a perfusion and suction system, which includes the following steps:

step 1), preset a highest warning pressure value, a lowest warning pressure value, a pressure control value and a perfusion flow gear;

step 2), the host controller controls the feeding of the perfusion solution in the perfusion unit and the suction of the suction unit; and step 3), the pressure detection device collects the intracavity pressure and transmits it to a host controller, and the host controller automatically adjusts the corresponding state system according to the real-time monitored pressure value and the data change trend of the pressure values, so that the current intracavity pressure is balanced at the pressure control value; when the data exceeds a standard, the system will automatically adjust its own perfusion and suction status to reach a balanced state of perfusion and suction as soon as possible while maintaining a certain intracavity pressure; the perfusion parameters include a perfusion flow gear, and the suction parameters include an opening threshold of a relief valve and a suction pressure threshold;

The pressure regulation modes of the host controller include a coarse tuning mode, a fine tuning mode and a mixed tuning mode. The coarse tuning mode is in response to an extreme situation where the intracavity pressure is in an extreme condition, and the fine tuning mode is in response to a small pressure difference where the intracavity pressure deviates from the pressure control value; the mixed tuning mode is in response to the intracavity pressure not yet reaching an extreme condition and having a large deviation value. For example, when the pressure difference between the intracavity pressure and the pressure control value exceeds ±20 mmHg, the coarse tuning mode is activated; when the pressure difference exceeds ±3 mmHg and is within ±8 mmHg, the fine tuning mode is activated; when the detected pressure difference exceeds ±8 mmHg and is within ±20 mmHg, the mixed tuning mode is activated.

The pressure control value may be a point value or an interval value. In some embodiments of the present disclosure, as shown in FIGS. 2-4, the pressure control value is 10 mmHg, and when the difference between the intracavity pressure and the pressure control value is within ±3 mmHg, the pressure regulation process is started.

Figure 2:
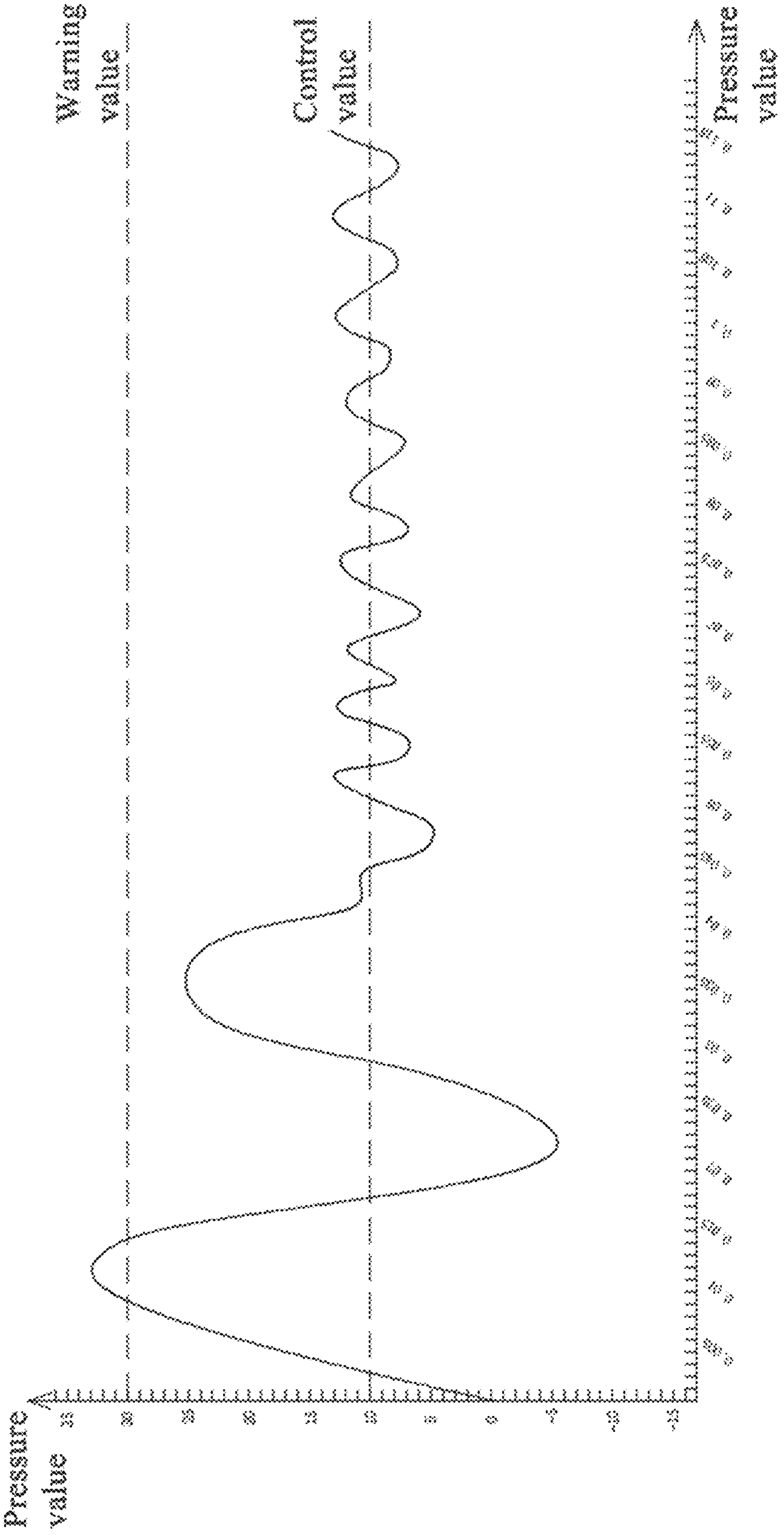
FIGS. 2-4 are process curve diagrams of the control method provided by the present disclosure.

As shown in FIG. 2, when it is detected that the intracavity pressure exceeds the highest warning line, i.e. the pressure difference between the intracavity pressure and the pressure control value is in an extreme situation, for example, greater than 20 mmHg, the coarse tuning mode is activated, and the host controller controls to lower the perfusion flow gear, controls the suction pressure threshold so that the suction flow rate is greater than the perfusion flow rate; when the pressure difference in the cavity exceeds the lowest warning line, the coarse tuning mode is activated, and the perfusion flow gear is tuned to the maximum, the relief valve will be opened, and the suction pressure threshold will be tuned to a threshold in a stable state, a rapid balance effect is achieved, so that the equipment can be free from the current state as soon as possible. In this way, the system response is accelerated and the static error is reduced. However, this tuning mode will increase the overshoot and deteriorate the stability. In this embodiment, the perfusion flow gear is adjusted to the lowest gear or the highest gear to speed up the pressure adjustment. At the same time, in order to avoid an excessive adjustment amplitude of the pressure, the suction pressure threshold is tuned to the suction pressure threshold in a stable state, which refers to the corresponding suction pressure threshold when the intracavity pressure recorded by the host controller reaches the pressure control value interval.

Figure 4:
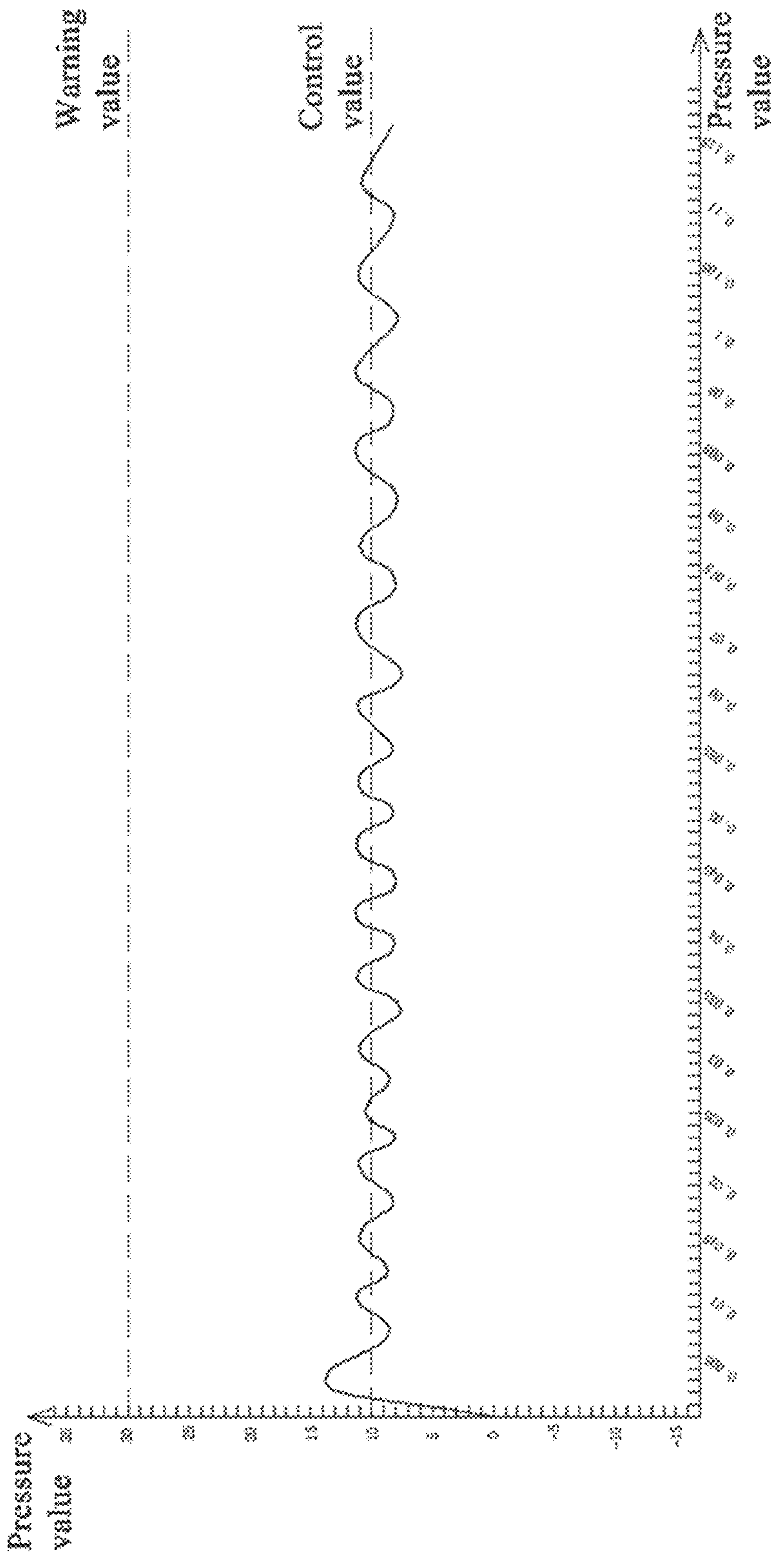

As shown in FIG. 4, when the detected pressure difference exceeds ±3 mmHg and is within ±8 mmHg, the fine tuning mode is activated, indicating that the pressure difference in the cavity is not large. In order to maintain the perfusion demand during operation and keep the perfusion flow rate unchanged, a dynamic balanced perfusion is achieved by controlling the suction pressure threshold, and the intracavity pressure is controlled at the "pressure control value". In this state, there is no need to adjust the perfusion or open the relief valve. This is because the two tuning modes will cause large fluctuations in data. It is also easy to upset the current dynamic balance. Therefore, at this stage, it is necessary to start the fine tuning mode of the system, maintaining the perfusion gear to maintain operation and keeping the relief valve closed, and performing pressure adjustment by finely tuning the suction pressure threshold. In addition, in the process of perfusion and suction, there are many tubelines in the cavity, the pressure fluctuation is large, and the frequency of pressure detection is fast. The setting of a suction pressure threshold also needs to be adjusted in real time according to the change trend of data. In an embodiment of the present disclosure, when the pressure difference exceeds-3 mmHg and is within −8 mmHg, keep the perfusion flow gear unchanged, keep the relief valve closed, maintain the current operation of perfusion, observe the change trend of uploaded data, increase the suction pressure threshold if it is in an ascending stage, decrease the suction pressure threshold if it is in a descending trend, and the reduction amplitude is greater than the amplitude of increasing the suction pressure threshold in the ascending stage; in this way, in the process of data adjustment, the suction pressure threshold tends to be decreased as a whole to achieve the effect of supercharging by fine tuning. When the pressure difference exceeds 3 mmHg and is within 8 mmHg, keep the perfusion operating at the current level; observe the change trend of uploaded data, increase the "suction pressure threshold" if it is in an ascending stage, decrease the "suction pressure threshold" if it is in a descending trend, and the reduction amplitude is smaller than the amplitude of increasing the suction pressure threshold in the ascending stage. In this way, in the process of data adjustment, the "suction pressure threshold" tends to be increased as a whole to achieve the effect of pressure reduction. Judge the state of the current detected pressure value and the data change trend, adjust the suction pressure threshold to make it increase or decrease, and reduce the damage to body cavity caused by large pressure fluctuation.

Figure 3:
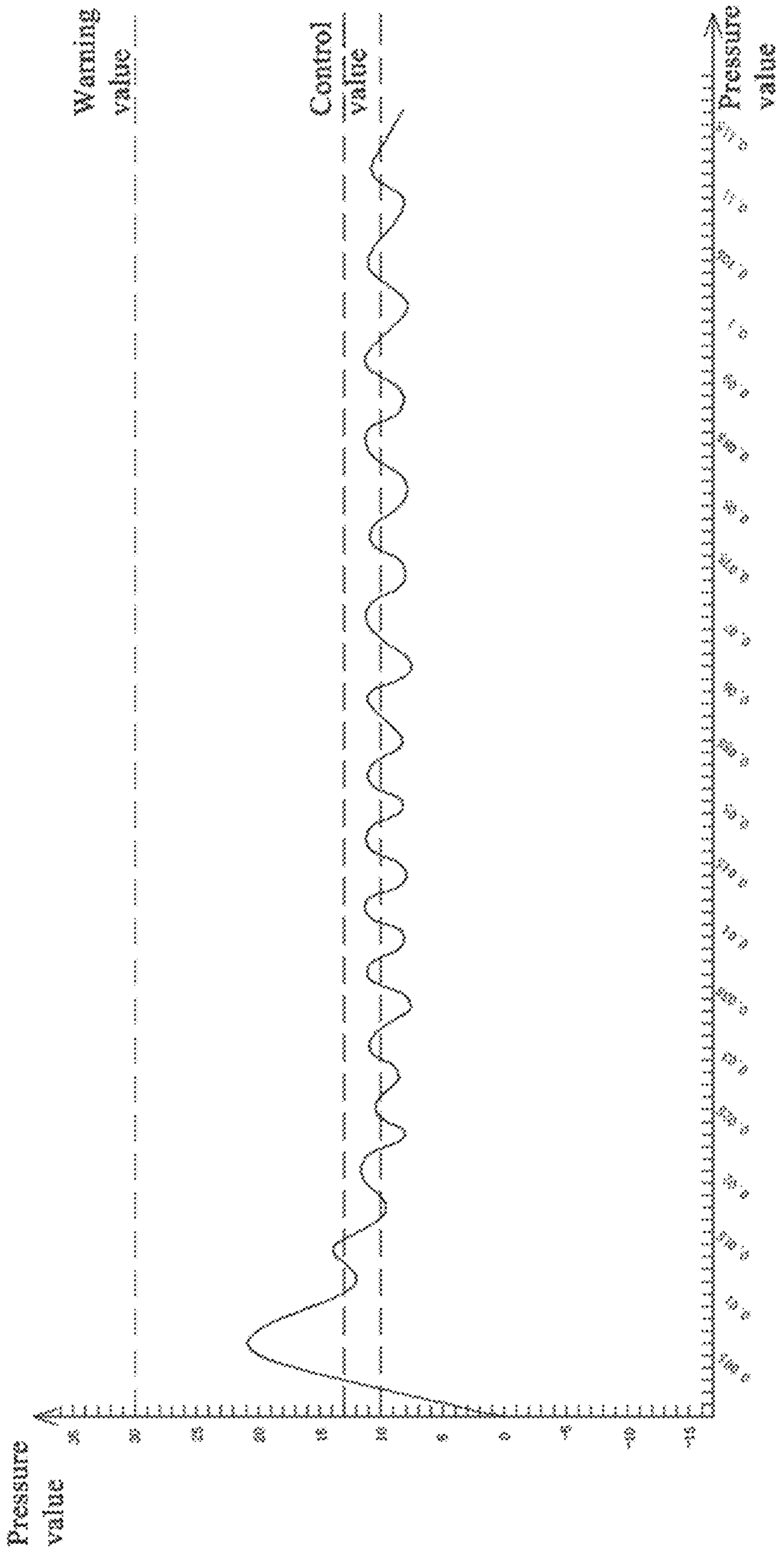

In some embodiments of the present disclosure, as shown in FIG. 3, when it is detected that the pressure difference exceeds ±8 mmHg and is within ±20 mmHg, a mixed tuning mode is activated, that is, combining fine tuning of the perfusion flow, fine tuning of the relief valve and fine tuning of the suction pressure threshold to jointly act on the intracavity pressure through jointly tuning the perfusion flow gear, the relief valve and the suction pressure threshold, so as to achieve the effect of supercharging or pressure reduction. Specifically, when the detected pressure difference exceeds 8 mmHg and is within 20 mmHg, appropriately reduce the perfusion flow rate, observe the change trend of uploaded data, increase the suction pressure threshold if it is in an ascending stage, and decrease the suction pressure threshold if it is in a descending state, and the reduction amplitude is smaller than the amplitude of increasing the suction pressure threshold in the ascending stage; in this way, in the process of data adjustment, the "suction pressure threshold" tends to be increased as a whole to achieve the effect of pressure reduction; when the pressure difference is detected lower than −8 mmHg and is within −20 mmHg, keep the perfusion flow rate at the current level, open the relief valve in stages, observe the change trend of uploaded data, increase the suction pressure threshold if it is in an ascending stage, decrease the "suction pressure threshold" if it is in a descending trend, and the reduction amplitude is greater than the amplitude of increasing the suction pressure threshold in the ascending stage; in this way, in the process of data adjustment, the "suction pressure threshold" tends to be decreased as a whole to achieve the effect of supercharging. In this embodiment, the amplitude of tuning the suction pressure threshold increases with an increase in the pressure difference between the intracavity pressure and the pressure control value. Thus, a combination of coarse tuning and fine tuning is realized through the amplitude of the suction pressure threshold, so that the intracavity pressure quickly reaches the pressure control value to avoid tissue damage caused by excessive pressure fluctuations in the body.

For example, the relationship between the negative pressure suction flow rate in ml/min corresponding to the suction pressure threshold value and is statistically analyzed and classified into 12 categories. They are at −5 mmhg, −10 mmhg, −15 mmhg, −20 mmhg, −25 mmhg, −30 mmhg, −35 mmhg, −40 mmhg, −45 mmhg, −50 mmhg, −60 mmhg and −70 mmhg, respectively. This value is generally used as the default initial value of the system when the system is started, which will be changed later with the dynamic balance process. The value of the balance point will be updated to achieve an effect of dynamic balance.

The pressure differences between the intracavity pressure and the pressure control value Pa in mmhg are counted and then classified. There are 13 states of the intracavity pressure: 1:>20, 2: 15<Pa<=20, 3: 10<Pa<=15, 4: 8<Pa<=10, 5: 5<Pa<=8, 6: 3<Pa<=5, 7: −3<Pa<=3, 8: −5<Pa<=−3, 9: −8<Pa<=−5, 10: −10<Pa<=−8, 11: −15<Pa<=−10, 12: −20<Pa<=−15 and 13: −20<Pa.

According to the above statistical classification, the newly collected intracavity pressure data is compared with the historical data, so as to quickly achieve the dynamic balance of perfusion and suction by adjusting the perfusion, suction and relief valves according to the change trend of historical data.

According to the pressure difference Pa in mmhg between the intracavity pressure and the pressure control value, this embodiment provides the following processing mode:

1. (Pa>20): the perfusion runs at the current gear−4, increase the suction pressure, and enhance the suction flow rate according to the negative pressure suction flow rate corresponding to the suction pressure threshold recorded, so that the suction flow rate is greater than the perfusion flow rate; observe the change trend of uploaded data. If it continues to rise, adjust the perfusion to the lowest level and the suction pressure threshold to a threshold of balanced state until the current intracavity pressure returns to the "pressure control value" and restore the perfusion flow rate. If it continues to decrease, adjust the perfusion flow rate according to the changing requirements and increase the suction pressure threshold to achieve the effect of pressure reduction;
2. (15<Pa<=20): the perfusion runs at the current gear−3, and observe the change trend of uploaded data. Increase the "suction pressure threshold +5" if it is in an ascending stage, decrease the "suction pressure threshold −2" if it is in a descending trend. In this way, in the process of data adjustment, the "suction pressure threshold" tends to be increased as a whole to achieve the effect of pressure reduction;
3. (10<Pa<=15): the perfusion runs at the current gear−2, and observe the change trend of uploaded data. Increase the "suction pressure threshold +5" if it is in an ascending stage, decrease the "suction pressure threshold −3" if it is in a descending trend. In this way, in the process of data adjustment, the "suction pressure threshold" tends to be increased as a whole to achieve the effect of pressure reduction;
4. (8<Pa<=10): the perfusion runs at the current gear−1, and observe the change trend of uploaded data. Increase the "suction pressure threshold +4" if it is in an ascending stage, decrease the "suction pressure threshold −1" if it is in a descending trend. In this way, in the process of data adjustment, the "suction pressure threshold" tends to be increased as a whole to achieve the effect of pressure reduction;
5. (5<Pa<=8): maintain the current operation of perfusion, and observe the change trend of uploaded data. Increase the "suction pressure threshold +3" if it is in an ascending stage, decrease the "suction pressure threshold −1" if it is in a descending trend. In this way, in the process of data adjustment, the "suction pressure threshold" tends to be increased as a whole to achieve the effect of pressure reduction;
6. (3<Pa<=5): observe the change trend of uploaded data. Increase the "suction pressure threshold +2" if it is in an ascending stage, decrease the "suction pressure threshold −1" if it is in a descending trend. In this way, in the process of data adjustment, the "suction pressure threshold" tends to be increased as a whole to achieve the effect of pressure reduction;
7. (−3<Pa<=3): keep the current state, start timing and record data. When a certain time is reached, record the current suction pressure threshold (i.e. the suction pressure threshold corresponding to the stable state) and update it in a real-time manner. When the state is destroyed, it shall be re-timed, and the changed saved value can be used for quick recovery of balance during a dynamic adjustment;
8. (−5<Pa<=−3): maintain the current operation of perfusion, and observe the change trend of uploaded data. Increase the "suction pressure threshold +1" if it is in an ascending stage, decrease the "suction pressure threshold −2" if it is in a descending trend. In this way, in the process of data adjustment, the "suction pressure threshold" tends to be decreased as a whole to achieve the effect of supercharging;
9. (−8<Pa<=−5): maintain the current operation of perfusion, and observe the change trend of uploaded data. Increase the "suction pressure threshold +1" if it is in an ascending stage, decrease the "suction pressure threshold −3" if it is in a descending trend. In this way, in the process of data adjustment, the "suction pressure threshold" tends to be decreased as a whole to achieve the effect of supercharging;
10. (−10<Pa<=−8): maintain the current operation of perfusion, open the relief valve in stages, and observe the change trend of uploaded data. Increase the "suction pressure threshold +1" if it is in an ascending stage, decrease the "suction pressure threshold −4" if it is in a descending trend. In this way, in the process of data adjustment, the "suction pressure threshold" tends to be decreased as a whole to achieve the effect of supercharging;
11. (−15<Pa<=−10): maintain the current operation of perfusion, open the relief valve in stages, and observe the change trend of uploaded data. Increase the "suction pressure threshold +3" if it is in an ascending stage, decrease the "suction pressure threshold −5" if it is in a descending trend. The "suction pressure threshold" tends to be decreased as a whole to achieve the effect of supercharging;
12. (−20<Pa<=−15): the perfusion runs at the current gear+3, open the relief valve and adjust the "suction pressure threshold" to a threshold in a stable state. observe the change trend of uploaded data. Increase the "suction pressure threshold +2" if it is in an ascending stage, decrease the "suction pressure threshold −5" if it is in a descending trend. In this way, in the process of data adjustment, the "suction pressure threshold" tends to be decreased as a whole to achieve the effect of supercharging; and
13. (Pa<−20): the perfusion runs at the current gear+4, open the relief valve and adjust the "suction pressure threshold" to a threshold in a stable state to achieve a rapid balance effect, so that the equipment can be free from the current state as soon as possible.

As above, through the analysis of historical data, the pressure value in the cavity, the pressure control value and the pressure threshold are analyzed to dynamically adjust the perfusion flow rate and the suction flow rate so as to achieve a balance of the intracavity pressure.

Embodiment 2

Figure 5:
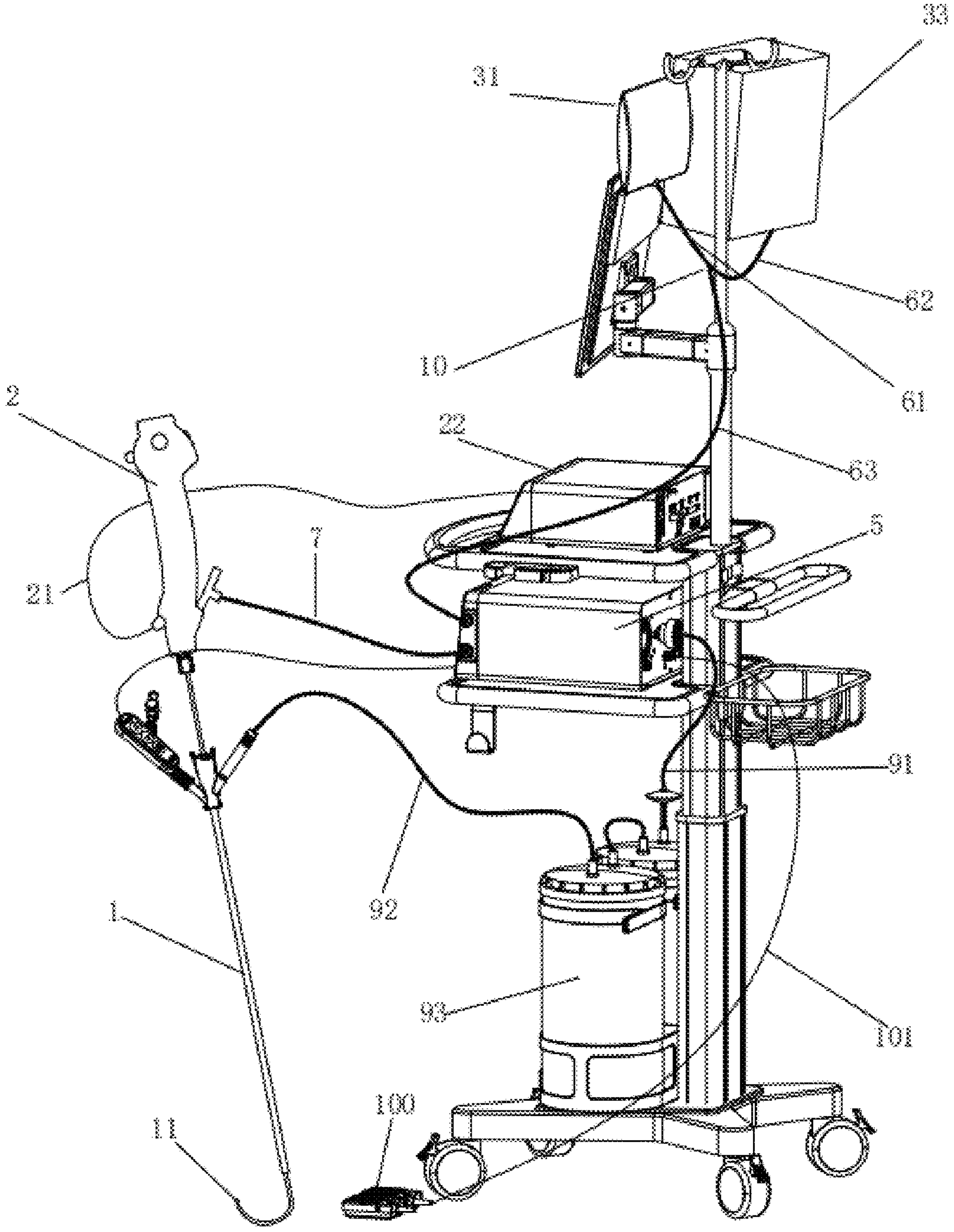
FIG. 5 is a structural schematic diagram of the perfusion and suction system provided by the present disclosure.

As shown in FIG. 5, on the basis of Embodiment 1, a perfusion unit in this embodiment includes a perfusion pump, a room-temperature liquid storage bag 31, a low-temperature liquid storage bag 33, a liquid inlet tube, a liquid outlet tube 7, and a temperature sensor 11.

A sheath tube 1 defines an instrument access channel to facilitate insertion of the endoscope 2. The sheath tube 1 provided in this embodiment is a three-channel sheath tube, with a central channel for inserting the endoscope 2, a pressure measuring channel and a suction channel for connecting with a suction unit. The endoscope 2 is inserted in the sheath tube 1. The camera at the head of the endoscope 2 is used to collect images in the cavity, and the images are processed by an image processor 22 and output to a display for physicians to observe the environment in the cavity. A liquid delivery channel is formed in the endoscope 2, which is used for the inflow of perfusion solution. Specifically, the endoscope 2 is connected with the image processor 22 through an endoscope harness 21.

The perfusion pump is used for pumping the perfusion solution; the room-temperature liquid storage bag 31 is used for storing the room-temperature perfusion solution; the low-temperature liquid storage bag 32 is used for storing the low-temperature perfusion solution, and the room-temperature liquid storage bag 31 and the low-temperature liquid storage bag 33 are connected with the perfusion pump through a liquid inlet tube; the perfusion pump is connected with the liquid delivery channel of the endoscope through the liquid outlet tube 7. The low-temperature liquid storage bag can be a liquid storage bag directly filled with low-temperature normal saline, or a room-temperature liquid storage bag that is placed in a refrigerator whose temperature can be adjusted. For example, the host controller controls the temperature of the refrigerator to obtain a low-temperature liquid storage bag.

A temperature sensor 11 is provided on an endoscope or a sheath tube to detect the temperature in a body cavity; the host controller controls a mixing ratio of the room-temperature perfusion solution to the low-temperature perfusion solution according to the temperature signal obtained by the temperature sensor, thereby controlling a supply temperature of the perfusion solution; in this way, when the temperature caused by laser lithotripsy is too high, the host controller controls the mixing ratio of room-temperature perfusion solution to the low-temperature perfusion solution, and sends the mixed perfusion solution with a predetermined temperature to the cavity such as the lesion site in the renal pelvis through the perfusion pump to take away the overheat generated during the lithotripsy process. In addition, the perfusion solution can wash away intraoperative bleeding and calculus powder, keep the field of vision of endoscope 2 clear, and also open the cavity to maintain the space necessary for the operation.

As the heat generated in the laser lithotripsy process is too high, the instantaneous heat of the laser will cause the liquid in the cavity to be boiling. In order to avoid tissue damage caused by the excessive temperature, the physician needs to adjust the rotation speed of the perfusion pump to increase the flow rate of the perfusion solution so as to take away the heat through a large flow rate of room-temperature perfusion solution. Excessive perfusion amount will cause excessive intracavity pressure. Therefore, the prior art requires relying on a suction unit to accelerate the circulation of the perfusion solution. However, even if a high-cycle perfusion method is adopted, the instantaneous pressure in the body is still at a high level and limited by the tubeline size of the liquid inlet tube and outlet tube, so the increase of its flow rate has limitations. In practice, even if the flow rate of room temperature perfusion solution at 25° C. is increased, it cannot reduce the temperature of boiling intracavity liquid in the perfusion and suction system to an appropriate and ideal value (30-40° C.) in time. The temperature control method provided in this embodiment can adjust the temperature of the perfusion solution in real time according to the difference between the collected temperature and the ideal temperature. First, it has the cleaning advantages of the room-temperature perfusion solution while achieving the purpose of temperature control, so as to avoid ignoring the perfusion advantages of the room-temperature perfusion solution when there is only low-temperature perfusion solution; second, when the temperature in the cavity is too high, low-temperature perfusion solution can be directly pumped into the cavity and the heat generated by the laser can be quickly taken away through the flow rate of the perfusion solution. In this way, the perfusion solution is cooled before being delivered to the liquid delivery channel to send the cooled liquid into the cavity to take away the heat. For example, the speed at which the liquid below 5° C. is sent into the liquid delivery channel to take away the heat is significantly faster than that of room-temperature perfusion solution, and the ideal temperature can be reached in a short time. It solves the technical problem of short operation course and slow cooling speed; third, with the pumping of low-temperature perfusion solution, the temperature in the cavity also begins to fall back and decrease. At this time, the mixing ratio of low-temperature perfusion solution to high-temperature perfusion solution is controlled according to the difference between the collected temperature and the ideal temperature, so that the temperature control process can stably reach the ideal temperature and avoid frostbite caused by supercooled liquid entering the body; the control method is firstly used to accurately control the temperature of the perfusion solution in the liquid inlet tube, and at the same time, the difference between the real-time temperature in the cavity and the ideal temperature is considered in the method to adjust the temperature of the perfusion solution in real time, and dynamically control the temperature of the lesion site in real time and accurately.

In some embodiments of the present disclosure, as shown in FIG. 5, the perfusion and suction system includes a room-temperature liquid storage bag 31, a low-temperature liquid storage bag 33, a room-temperature liquid inlet tube 61, a low-temperature liquid inlet tube 62, a mixing tubeline 63, and a proportion control valve 10. The room-temperature liquid storage bag 31 stores room-temperature perfusion solution; the low-temperature liquid storage bag 33 is configured to store a low-temperature perfusion solution; the room-temperature liquid storage bag 31 is connected with a room-temperature liquid inlet tube 61; the low-temperature liquid storage bag 33 is connected with the low-temperature liquid inlet tube 62, one end of the mixing tubeline 63 communicates with outlets of the room-temperature liquid inlet tube 61 and the low-temperature liquid inlet tube 62, and the other end thereof is connected with a perfusion pump. The proportion control valve 10 is used for controlling the flow rate of the liquid in the room-temperature liquid inlet tube 61 and the low-temperature liquid inlet tube 62. In this way, the temperature of the perfusion solution and the temperature in the cavity can be precisely regulated by the perfusion and suction system. In the first embodiment, a physician may connect the room-temperature liquid storage bag 31 and the mixing tubeline 63 through the proportion control valve 10, so that the room-temperature perfusion solution can be directly delivered into the cavity to clean off intraoperative bleeding, calculus powder, etc. In the second embodiment, a physician may communicate the low-temperature liquid storage bag 33 with the mixing tubeline 63 through the proportion control valve 10. Thus, when laser lithotripsy causes excessive temperature at the lesion site, for example, the liquid in the cavity boils directly, the low-temperature perfusion solution is sent directly into the cavity through the proportion control valve to quickly take away the heat generated by the laser. In the third embodiment, as the perfusion solution is injected, the temperature difference between the intracavity temperature and the ideal temperature gradually decreases. To avoid overcooling of the liquid in the cavity, the physician may adjust the proportion control valve 10 according to the temperature difference between the intracavity temperature and the ideal temperature so that the mixed perfusion solution with a specific temperature can be delivered into the delivery channel based on the mixing ratio of the room-temperature perfusion solution to the low-temperature perfusion solution, thus avoiding technical problems caused by overcooling or overheating of the perfusion solution. Accurate temperature control is then realized.

Alternatively, the room-temperature liquid inlet tube 61 and the low-temperature liquid inlet tube 62 are respectively provided with a proportion control valve 10. In this embodiment, the proportion control valve 10 is a three-way valve which connects the room-temperature liquid inlet tube 61 with the low-temperature liquid inlet tube 62 and the mixing tubeline 63, so that the above mentioned temperature control process can be realized.

Specifically, the three-way valve is a PID control valve.

This embodiment provides a temperature control method for a perfusion and suction system, including the steps of:

step 1), preset a first predetermined temperature $T_{max}$ and a second predetermined temperature $T_{min}$, i.e. establishing a standard ideal temperature range; the room-temperature storage liquid has a first preset temperature t1, and the low-temperature storage liquid has a second preset temperature t2; specifically, $T_{max}$ is 40° C., $T_{min}$ is 30° C., the first preset temperature t1 is 25° C., and the second preset temperature t2 is 0-5° C.

step 2), after each temperature acquisition, the host controller compares the acquired temperature T with the first predetermined temperature $T_{max}$ and the second predetermined temperature $T_{min}$. If the acquired temperature T is higher than the first predetermined temperature $T_{max}$, the control valve communicates the low-temperature liquid storage bag 33 with the mixing tubeline 63 or controls the mixing ratio of the room-temperature liquid inlet tube 61 to the low-temperature liquid inlet tube 62 according to the temperature difference between the acquired temperature and a desired temperature, in turn controlling the output liquid temperature of mixing tubeline 63. If the acquired temperature T is lower than the second predetermined temperature $T_{min}$, the control valve communicates the room-temperature liquid storage bag 31 with the mixing tubeline 63 or controls the mixing ratio of the room-temperature liquid inlet tube 61 to the low-temperature liquid inlet tube 62; and step 3) If it is judged that the acquired temperature T is between 30° C. and 40° C. after reaching the ideal temperature, the temperature control process will be stopped; if not, the opening degree of the proportion control valve 10 will be further adjusted in real time according to the temperature difference between the acquired temperature T and the ideal temperature until the ideal temperature is reached, so as to obtain a dynamic balance of temperature.

In the prior art, the heat in the cavity is quickly taken away by accelerating the number of cycles of perfusion flow and suction flow while avoiding the damage caused by excessively high perfusion pressure. The low-temperature perfusion solution provided in this embodiment can realize a small flow rate of the perfusion solution without causing excessive pressure problems.

It can be understood that, compared with the existing perfusion and suction system, the perfusion and suction system provided in this embodiment significantly reduces the number of cycles and liquid flow rate due to the controllable temperature of the perfusion solution, avoids tissue damage caused by high-flow and high-pressure, and has a gentler and more fine surgical process and controllable temperature.

The temperature sensor 11 is assembled on the endoscope 2 or the sheath tube 1. In this embodiment, the temperature sensor 11 is installed at the head end of the endoscope to collect the temperature in the cavity in real time. The temperature measuring signal can be directly fed back to the host controller; it can also be transmitted to the main body of the electronic endoscope 2, and then the main body of the electronic endoscope 2 feeds back signals to the perfusion and suction host. The temperature of human lesions can be detected in real time.

In one embodiment of the present disclosure, as shown in FIG. 5, the proportion control valve 10 is disposed in a perfusion and suction host so as to shorten the travel distance of low-temperature perfusion solution.

Figure 6:
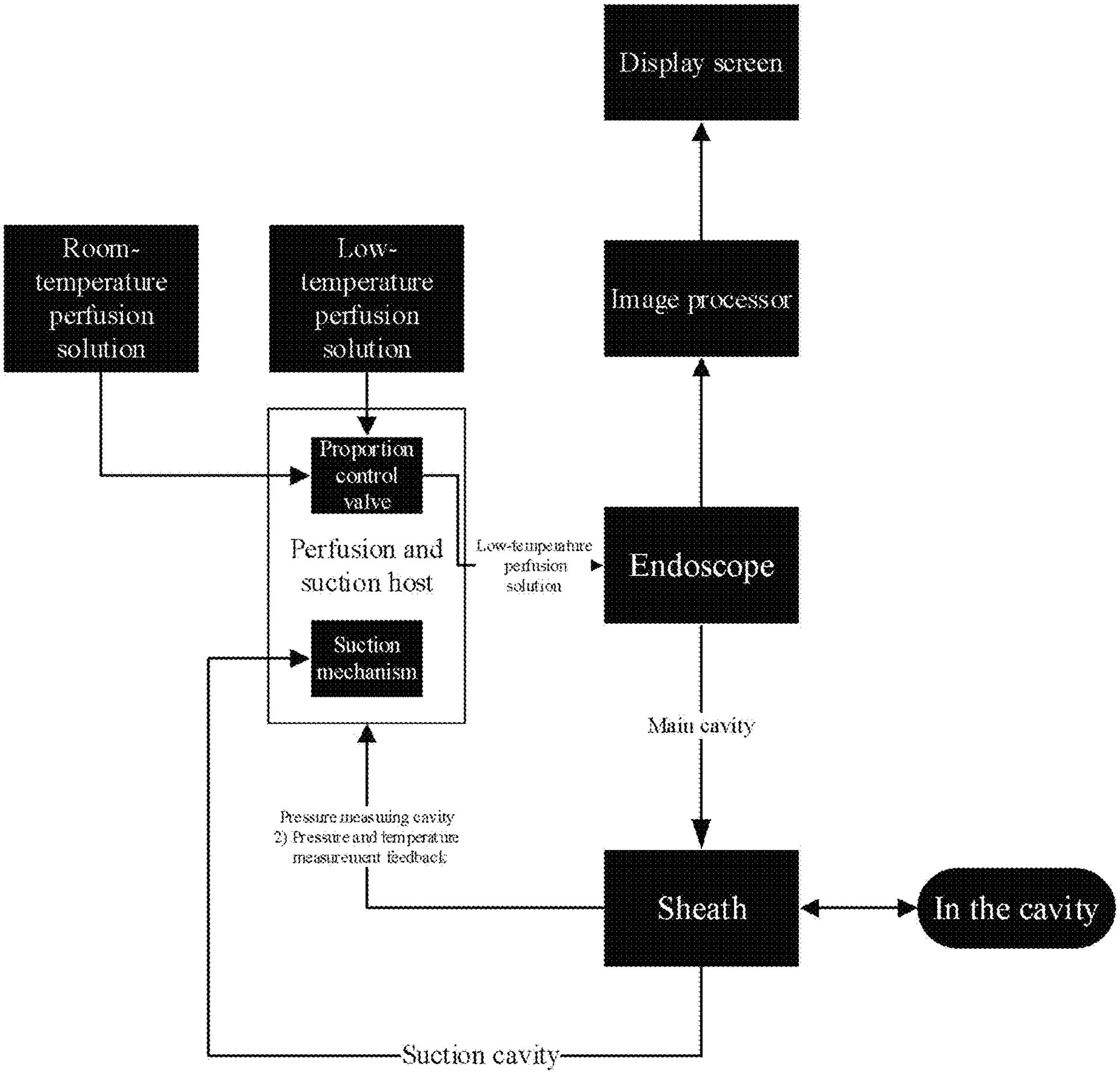
FIG. 6 is a schematic diagram for the working principle of the perfusion and suction system provided by the present disclosure.
Figure 7:
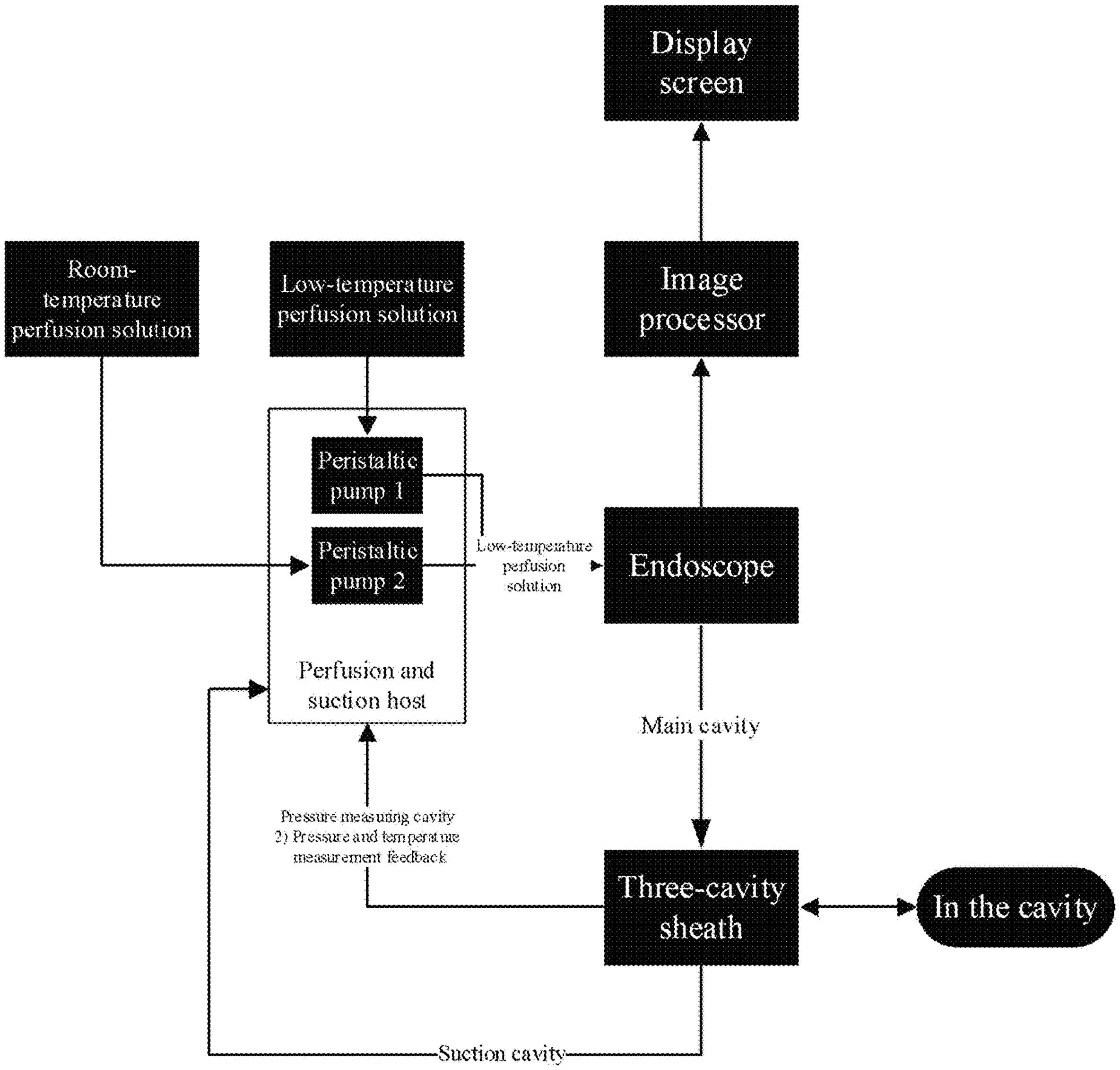
FIG. 7 is a schematic diagram for the working principle of the perfusion and suction system provided by the present disclosure.

In other specific embodiments of the present disclosure, as shown in FIG. 6, the perfusion and suction system includes a low-temperature perfusion pump and a high-temperature perfusion pump. The low-temperature perfusion pump is connected with the low-temperature liquid inlet tube 62, the room-temperature perfusion pump is connected with the room-temperature liquid inlet tube, and the room-temperature perfusion pump is connected with the liquid outlet tube after converging with the liquid outlet of the low-temperature perfusion pump, so that the rotation speed ratio between the room-temperature perfusion pump to the low-temperature perfusion pump can be adjusted in real time according to the temperature difference between the acquired temperature and the ideal temperature, and a variety of perfusion methods can also be realized. Specifically, the low-temperature perfusion pump and the high-temperature perfusion pump are both peristaltic pumps, and the temperature and flow rate of the mixed perfusion solution are controlled by adjusting the rotation speed ratio of 2 sets of peristaltic pumps respectively through the perfusion suction host.

This embodiment further provides a temperature control method for a perfusion and suction system, including the steps of:

step 1), preset a first predetermined temperature $T_{max}$ and a second predetermined temperature $T_{min}$, wherein the room-temperature storage liquid has a first predetermined temperature t1 and the low-temperature storage liquid has a second predetermined temperature t2;

step 2), after each temperature acquisition, compare the acquired temperature T with the first predetermined temperature $T_{max}$ and the second predetermined temperature $T_{min}$; if the acquired temperature T is higher than the first predetermined temperature $T_{max}$ or lower than the second predetermined temperature $T_{min}$, the host controller controls the rotation speed ratio of the room-temperature perfusion pump to the low-temperature perfusion pump respectively to adjust the flow rates of the room-temperature liquid inlet tube 61 and the low-temperature liquid inlet tube 62; and step 3), if it is judged that T reaches an ideal temperature, the temperature control process will be stopped; if not, the rotation speed ratio of the room-temperature perfusion pump to the low-temperature perfusion pump will be further adjusted in real time according to the temperature difference until the ideal temperature is reached.

In this embodiment, the perfusion pump and the diaphragm pump of the suction unit are integrated with a host controller. The perfusion and suction host is used to control the flow rate and pressure of perfusion and suction as well as the temperature of the perfusion solution, so that the equipment is more simplified and easy to operate. In order to cool the liquid in the tubeline, the liquid inlet tube and outlet tube can be wrapped with thermal insulation materials.

Alternatively, the host controller is connected with the footrest 100 through a footrest cable 101, and it is difficult for a physician to operate by hand during surgical operation. The host controller can control the perfusion and suction system through the footrest.

In this embodiment, as shown in FIG. 4 to FIG. 6, the system provided by the present disclosure adjusts the pressure, flow rate and temperature of perfusion in a timely manner through dual monitoring of the pressure and temperature in the cavity, thereby effectively improving the safety of surgery and reducing the risk caused by excessively high or low temperature and pressure during surgery.

The perfusion and suction system provided by the present disclosure realizes accurate control of the temperature in the cavity by controlling the temperature of the perfusion solution at the source. Compared with only relying on the adjustment of perfusion flow rate, this embodiment first reduces the excessive requirement for perfusion flow rate and controls the temperature more accurately and in real time, thus reducing the experience requirements of the surgeon and reducing postoperative complications.

What is claimed is:

1. A perfusion and suction system, comprising:

a sheath tube, an endoscope, a perfusion unit, a suction unit, a host controller and a pressure sensor, wherein a suction channel is provided in the sheath tube, the endoscope is inserted in the sheath tube, and a liquid delivery channel is formed in the endoscope; the pressure sensor is disposed in the endoscope, the sheath tube or a perfusion pump, the pressure sensor is used for detecting a pressure inside a body cavity, and the perfusion unit communicates with the liquid delivery channel for injecting a perfusion solution into the body cavity; the suction unit comprises a suction pump and a suction container connected to the suction pump, the suction container is provided with a pressure relief valve, the suction container communicates with the suction channel for sucking out liquid in the body cavity, and the perfusion unit cooperates with the suction unit to keep the body cavity at an appropriate pressure; the host controller is communicatively connected with the pressure sensor, the perfusion unit and the suction unit;

the host controller is configured to execute a constant pressure control method, and the constant pressure control method comprises the following steps:

step 1), presetting a highest warning pressure value, a lowest warning pressure value, a pressure control value and a perfusion flow gear;

step 2), the host controller controlling the perfusion unit to send the perfusion solution into the body cavity, and controlling the suction unit to pump out the liquid in the body cavity; and step 3), a pressure detection device collecting the pressure in the body cavity and transmitting it to the host controller, wherein the host controller adjusts perfusion parameters and suction parameters according to a real-time monitored pressure value and a data change trend of a pressure value, so that an intracavity pressure is balanced at the pressure control value, thus realizing a balance state between perfusion and suction; the perfusion parameters include a perfusion flow gear, and the suction parameters include an opening threshold of a relief valve and a suction pressure threshold; the suction pressure threshold is a suction pressure threshold of the suction container preset by the host controller, and on-off of the suction pump is controlled by setting the suction pressure threshold;

the constant pressure control of the host controller comprises a coarse tuning mode, a fine tuning mode and a mixed tuning mode, the coarse tuning mode is in response to the intracavity pressure exceeding the highest warning pressure value and the lowest warning pressure value; the fine tuning mode is in response to a pressure difference between the intracavity pressure and the pressure control value being at a first level; the mixed tuning mode is in response to the pressure difference between the intracavity pressure and the pressure control value being at a second level, and the pressure difference at the second level is greater than the pressure difference at the first level;

the coarse tuning mode comprises steps of tuning the perfusion flow gear and a way to open the relief valve in response to the intracavity pressure exceeding the highest warning pressure value and the lowest warning pressure value;

the fine tuning mode comprises steps of maintaining the perfusion flow gear to maintain operation and keeping the relief valve closed, and performing pressure adjustment by finely tuning the suction pressure threshold; and the mixed tuning mode comprises steps of combining fine tuning of the perfusion flow gear, fine tuning of the relief valve and fine tuning of the suction pressure threshold to jointly act on the intracavity pressure through jointly tuning the perfusion flow gear, the relief valve and the suction pressure threshold, so as to achieve an effect of supercharging or pressure reduction.

2. The perfusion and suction system according to claim 1, wherein when the pressure difference between the intracavity pressure and the pressure control value exceeds ±20 mmHg, the coarse tuning mode is activated; when the pressure difference exceeds ±3 mmHg and is within ±8 mmHg, the fine tuning mode is activated; when the detected pressure difference exceeds ±8 mmHg and is within ±20 mmHg, the mixed tuning mode is activated.

3. The perfusion and suction system according to claim 1, wherein the coarse tuning mode comprises steps: when the pressure value in the body cavity exceeds the highest warning pressure value, the host controller controls to lower the perfusion flow gear, controls the suction pressure threshold so that a suction flow rate is greater than a perfusion flow rate; when the pressure difference in the body cavity exceeds the lowest warning pressure value, the perfusion flow gear is increased, the relief valve is opened, and the suction pressure threshold is tuned to a threshold in a stable state, a rapid balance effect is achieved, so that the intracavity pressure is free from an extreme state.

4. The perfusion and suction system according to claim 2, wherein when the pressure difference exceeds −3 mmHg and is within −8 mmHg, the perfusion flow gear is kept unchanged, the relief valve is kept closed, a current operation of perfusion is maintained, a change trend of uploaded data is observed, the suction pressure threshold is increased if it is in an ascending stage, the suction pressure threshold is decreased if it is in a descending trend, and a reduction amplitude is greater than an increasing amplitude of the suction pressure threshold in the ascending stage; in a process of data adjustment, the suction pressure threshold tends to be decreased as a whole to achieve the effect of supercharging by fine tuning; when the pressure difference exceeds 3 mmHg and is within 8 mmHg, the perfusion operating is kept at a current level; the change trend of the uploaded data is observed, the suction pressure threshold is increased if it is in the ascending stage, the suction pressure threshold is decreased if it is in the descending trend, and the reduction amplitude is smaller than the increasing amplitude of the suction pressure threshold in the ascending stage; in the process of data adjustment, the suction pressure threshold tends to be increased as a whole to achieve the effect of pressure reduction.

5. The perfusion and suction system according to claim 2, wherein when the detected pressure difference exceeds 8 mmHg and is within 20 mmHg, the perfusion flow rate is reduced, a change trend of uploaded data is observed, the suction pressure threshold is increased if it is in an ascending stage, and the suction pressure threshold is decreased if it is in a descending state, and the reduction amplitude is smaller than the increasing amplitude of the suction pressure threshold in an ascending stage; in a process of data adjustment, the suction pressure threshold tends to be increased as a whole to achieve an effect of pressure reduction; when the pressure difference is detected lower than −8 mmHg and is within −20 mmHg, the perfusion flow rate is kept at a current level, the relief valve is opened in stages, the change trend of the uploaded data is observed, the suction pressure threshold is increased if it is in the ascending stage, the suction pressure threshold is decreased if it is in the descending trend, and the reduction amplitude is greater than the increasing amplitude of the suction pressure threshold in the ascending stage; in the process of data adjustment, the suction pressure threshold tends to be decreased as a whole to achieve an effect of supercharging.

6. The perfusion and suction system according to claim 1, wherein a tuning amplitude of the suction pressure threshold increases with an increase in the pressure difference between the intracavity pressure and the pressure control value.

7. The perfusion and suction system according to claim 1, wherein the perfusion unit further comprises:

a perfusion pump for pumping the perfusion solution;

a room-temperature liquid storage bag for storing a room-temperature perfusion solution;

a low-temperature liquid storage bag for storing a low-temperature perfusion solution;

a room-temperature liquid inlet tube, with the room-temperature liquid storage bag being connected with the room-temperature liquid inlet tube;

a low-temperature liquid inlet tube, with the low-temperature liquid storage bag being connected with the low-temperature liquid inlet tube;

a temperature sensor provided on the endoscope or the sheath tube to detect a temperature in the body cavity;

a mixing tubeline, one end of the mixing tubeline being communicated with outlets of the room-temperature liquid inlet tube and the low-temperature liquid inlet tube, and the other end of the mixing tubeline being connected with the perfusion pump;

a proportion control valve for controlling liquid flow rates of the room-temperature liquid inlet tube and the low-temperature liquid inlet tube;

the host controller controls a mixing ratio of the room-temperature perfusion solution and the low-temperature perfusion solution according to a temperature signal obtained by the temperature sensor, thereby controlling a supply temperature of the perfusion solution;

the host controller is configured to execute a temperature control method, wherein the temperature control method comprises:

step 1), presetting a first predetermined temperature $T_{max}$ and a second predetermined temperature $T_{min}$, wherein the room-temperature perfusion solution has a first predetermined temperature t1 and the low-temperature perfusion solution has a second predetermined temperature t2;

step 2), after each temperature acquisition, comparing an acquired temperature T with the first predetermined temperature $T_{max}$ and the second predetermined temperature $T_{min}$; if the acquired temperature T is higher than the first predetermined temperature $T_{max}$ or lower than the second predetermined temperature $T_{min}$, the proportion control valve connects the room-temperature liquid storage bag with the mixing tubeline, connects the low-temperature liquid storage bag with the mixing tubeline, or controls the mixing ratio of the room-temperature liquid inlet tube and the low-temperature liquid inlet tube according to the temperature difference between the acquired temperature and a desired temperature, further controlling an output liquid temperature of the mixing tubeline; and step 3) if the acquired temperature T reaches an ideal temperature, a temperature control process is stopped; if the acquired temperature T does not reach the ideal temperature, an opening of the proportion control valve is further adjusted in real time according to a temperature difference until the ideal temperature is reached.

8. The perfusion and suction system according to claim 1, wherein the perfusion unit comprises:

a low-temperature perfusion pump connected with a low-temperature liquid inlet tube;

a room-temperature perfusion pump connected with a room-temperature liquid inlet tube, and communicated with a liquid outlet tube after being merged with a liquid outlet of the low-temperature perfusion pump;

the host controller is configured to execute a temperature control method, wherein the temperature control method comprises:

step 1), presetting a first predetermined temperature $T_{max}$ and a second predetermined temperature $T_{min}$, wherein a room-temperature storage liquid has a first predetermined temperature t1 and a low-temperature storage liquid has a second predetermined temperature t2;

step 2), after each temperature acquisition, comparing the acquired temperature T with the first predetermined temperature $T_{max}$ and the second predetermined temperature $T_{min}$; if the acquired temperature T is higher than the first predetermined temperature $T_{max}$ or lower than the second predetermined temperature $T_{min}$, the host controller controls a rotation speed ratio of the room-temperature perfusion pump to the low-temperature perfusion pump respectively to adjust flow rates of the room-temperature liquid inlet tube and the low-temperature liquid inlet tube; and step 3), if the acquired temperature T reaches an ideal temperature, a temperature control process is stopped; if the acquired temperature T does not reach the ideal temperature, the rotation speed ratio of the room-temperature perfusion pump to the low-temperature perfusion pump is further adjusted in real time according to a temperature difference until the ideal temperature is reached.

9. A perfusion and suction container, comprising;

a perfusion unit, comprising a perfusion pump for pumping a perfusion solution;

a room-temperature liquid storage bag for storing a room-temperature perfusion solution;

a low-temperature liquid storage bag for storing a low-temperature perfusion solution;

a room-temperature liquid inlet tube, with the room-temperature liquid storage bag being connected with the room-temperature liquid inlet tube;

a low-temperature liquid inlet tube, with the low-temperature liquid storage bag being connected with the low-temperature liquid inlet tube;

a suction unit comprises a suction pump, a first negative pressure suction tube, a suction container and a second negative pressure suction tube, wherein one end of the first negative pressure suction tube is connected with the suction pump and an other end of the first negative pressure suction tube is connected with the suction container, and one end of the second negative pressure suction tube is connected with the suction container and the other end of the second negative pressure suction tube is connected with a sheath tube;

a host controller communicatively connected with the perfusion unit and the suction unit, wherein the host controller is configured to execute the constant pressure control method according to claim 1.

10. The perfusion and suction container according to claim 9, wherein the perfusion pump, a diaphragm pump and the host controller are integrated.

* * * * *